United States Patent [19]
Reber et al.

[11] Patent Number: 5,961,451
[45] Date of Patent: Oct. 5, 1999

[54] NONINVASIVE APPARATUS HAVING A RETAINING MEMBER TO RETAIN A REMOVABLE BIOSENSOR

[75] Inventors: William L. Reber, Schaumburg; Jeffrey G. Toler, Algonquin, both of Ill.; Cary D. Perttunen, Shelby Township, Mich.

[73] Assignee: Motorola, Inc., Schaumburg, Ill.

[21] Appl. No.: 08/833,566

[22] Filed: Apr. 7, 1997

[51] Int. Cl.$^6$ ........................................................ A61B 5/00
[52] U.S. Cl. ........................ 600/322; 600/316; 600/310; 250/341.1
[58] Field of Search ........................ 600/309, 322, 600/346, 347, 572, 573, 578, 314, 316, 575, 583, 584, 562, 310; 604/290, 313; 436/95; 250/341.1; 422/99, 82.05

[56] References Cited

U.S. PATENT DOCUMENTS

| | | |
|---|---|---|
| 4,014,321 | 3/1977 | March . |
| 4,655,225 | 4/1987 | Dahne et al. . |
| 4,750,496 | 6/1988 | Reinhart et al. . |
| 4,875,486 | 10/1989 | Rapoport et al. . |
| 4,882,492 | 11/1989 | Schlager . |
| 4,921,728 | 5/1990 | Takiguchi et al. . |
| 5,009,230 | 4/1991 | Hutchinson . |
| 5,019,974 | 5/1991 | Beckers ............................. 364/413.02 |
| 5,028,787 | 7/1991 | Rosenthal et al. . |
| 5,036,861 | 8/1991 | Sembrowich et al. .................. 600/573 |
| 5,070,874 | 12/1991 | Barnes et al. . |
| 5,074,977 | 12/1991 | Cheung et al. . |
| 5,077,476 | 12/1991 | Rosenthal . |
| 5,086,229 | 2/1992 | Rosenthal et al. . |
| 5,110,833 | 5/1992 | Mosbach . |
| 5,112,124 | 5/1992 | Harjunmaa et al. . |
| 5,119,819 | 6/1992 | Thomas et al. . |
| 5,137,023 | 8/1992 | Mendelson et al. . |
| 5,222,496 | 6/1993 | Clarke et al. . |
| 5,233,997 | 8/1993 | Klein et al. . |
| 5,237,178 | 8/1993 | Rosenthal et al. . |
| 5,243,983 | 9/1993 | Tarr et al. . |
| 5,267,152 | 11/1993 | Yang et al. . |
| 5,297,548 | 3/1994 | Pologe ..................................... 600/322 |
| 5,310,648 | 5/1994 | Arnold et al. . |
| 5,313,941 | 5/1994 | Braig et al. ............................. 600/322 |
| 5,321,265 | 6/1994 | Block . |
| 5,361,758 | 11/1994 | Hall et al. . |
| 5,370,114 | 12/1994 | Wong et al. . |
| 5,379,764 | 1/1995 | Barnes et al. . |
| 5,383,452 | 1/1995 | Buchert . |
| 5,398,681 | 3/1995 | Kupershmidt . |
| 5,424,545 | 6/1995 | Block et al. . |
| 5,433,197 | 7/1995 | Stark . |
| 5,434,412 | 7/1995 | Sodickson et al. . |
| 5,438,201 | 8/1995 | Rosenthal et al. . |
| 5,448,992 | 9/1995 | Kupershmidt . |
| 5,458,140 | 10/1995 | Eppstein et al. ......................... 600/573 |
| 5,459,317 | 10/1995 | Small et al. . |
| 5,492,118 | 2/1996 | Gratton et al. . |
| 5,497,772 | 3/1996 | Schulman et al. ...................... 600/347 |
| 5,507,288 | 4/1996 | Bocker et al. ........................... 600/322 |
| 5,508,203 | 4/1996 | Fuller et al. ............................. 436/149 |
| 5,580,794 | 12/1996 | Allen ....................................... 436/169 |
| 5,601,079 | 2/1997 | Wong et al. ............................. 600/322 |
| 5,617,851 | 4/1997 | Lipkovker ............................... 600/573 |
| 5,617,852 | 4/1997 | MacGregor ............................. 600/322 |
| 5,618,275 | 4/1997 | Bock ....................................... 604/290 |
| 5,714,123 | 2/1998 | Sohrab ..................................... 422/99 |
| 5,728,352 | 3/1998 | Poto et al. ............................. 422/82.05 |

*Primary Examiner*—Richard J. Apley
*Assistant Examiner*—Justine R. Yu
*Attorney, Agent, or Firm*—Jeffrey G. Toler; James E. Gauger

[57] ABSTRACT

In accordance with a first aspect, a noninvasive apparatus comprises a housing (42) having a grasping region (44), and a noninvasive extraction device (10) to noninvasively extract a sample from a hand of an end user at the grasping region (44). In accordance with a second aspect, a noninvasive apparatus comprises a card-shaped housing which supports the noninvasive extraction device 10. In accordance with a third aspect, a retaining member (22) retains a removable biosensor (16) proximate to at least a portion of the noninvasive extraction device (10).

9 Claims, 5 Drawing Sheets

NONINVASIVE APPARATUS HAVING A RETAINING MEMBER TO RETAIN A REMOVABLE BIOSENSOR

TECHNICAL FIELD

The present invention relates to methods and systems to noninvasively extract biological samples.

BACKGROUND OF THE INVENTION

Many diagnostic devices and methods perform an invasive test requiring a blood sample to be extracted from an end user. For example, most commercially-available portable blood glucose meters require an end user to prick his/her finger with a lancet to perform a blood glucose level test. After pricking his/her finger, the end user deposits a drop of blood onto a test strip. The sample of blood on the test strip is tested by the glucose meter to determine a glucose level. Since a typical end user with diabetes performs the above-described invasive test four times a day, the need exists for a noninvasive apparatus to perform blood glucose level tests.

HIV testing is another diagnostic procedure which uses an invasively-extracted sample of blood. This procedure and other diagnostic procedures also would benefit from a noninvasive apparatus designed therefor.

SUMMARY OF THE INVENTION

The present invention provides an apparatus comprising a noninvasive extraction device and a retaining member. The noninvasive extraction device is to noninvasively extract a biological sample. The retaining member is to retain a removable biosensor proximate to at least a portion of the noninvasive extraction device. The retaining member covers a first portion of a surface of the removable biosensor while externally exposing a second portion of the surface of the removable biosensor for user contact. The removable biosensor is to sense a characteristic of the biological sample.

The present invention further provides an apparatus comprising a card-shaped housing having a grasping region, a noninvasive extraction device to noninvasively extract a biological sample from a portion of a hand grasping the card-shaped housing at the grasping region, and a retaining member to retain a removable biosensor proximate to at least a portion of the noninvasive extraction device. The retaining member is to cover a first portion of a surface of the removable biosensor while exposing a second portion of the surface of the removable biosensor for contact by the portion of the hand. The removable biosensor is to sense a characteristic of the biological sample.

The present invention still further provides an apparatus comprising a housing and a noninvasive extraction device. The housing has a grasping region. The noninvasive extraction device is to noninvasively extract a biological sample from a portion of a hand grasping the housing at the grasping region.

The present invention yet still further provides an apparatus having a noninvasive extraction device supported by a card-shaped housing. The noninvasive extraction device is to noninvasively extract a biological sample.

BRIEF DESCRIPTION OF THE DRAWINGS

The invention is pointed out with particularity in the appended claims. However, other features of the invention are described in the following detailed description in conjunction with the accompanying drawings in which:

DETAILED DESCRIPTION OF A PREFERRED EMBODIMENT

Figure 1:
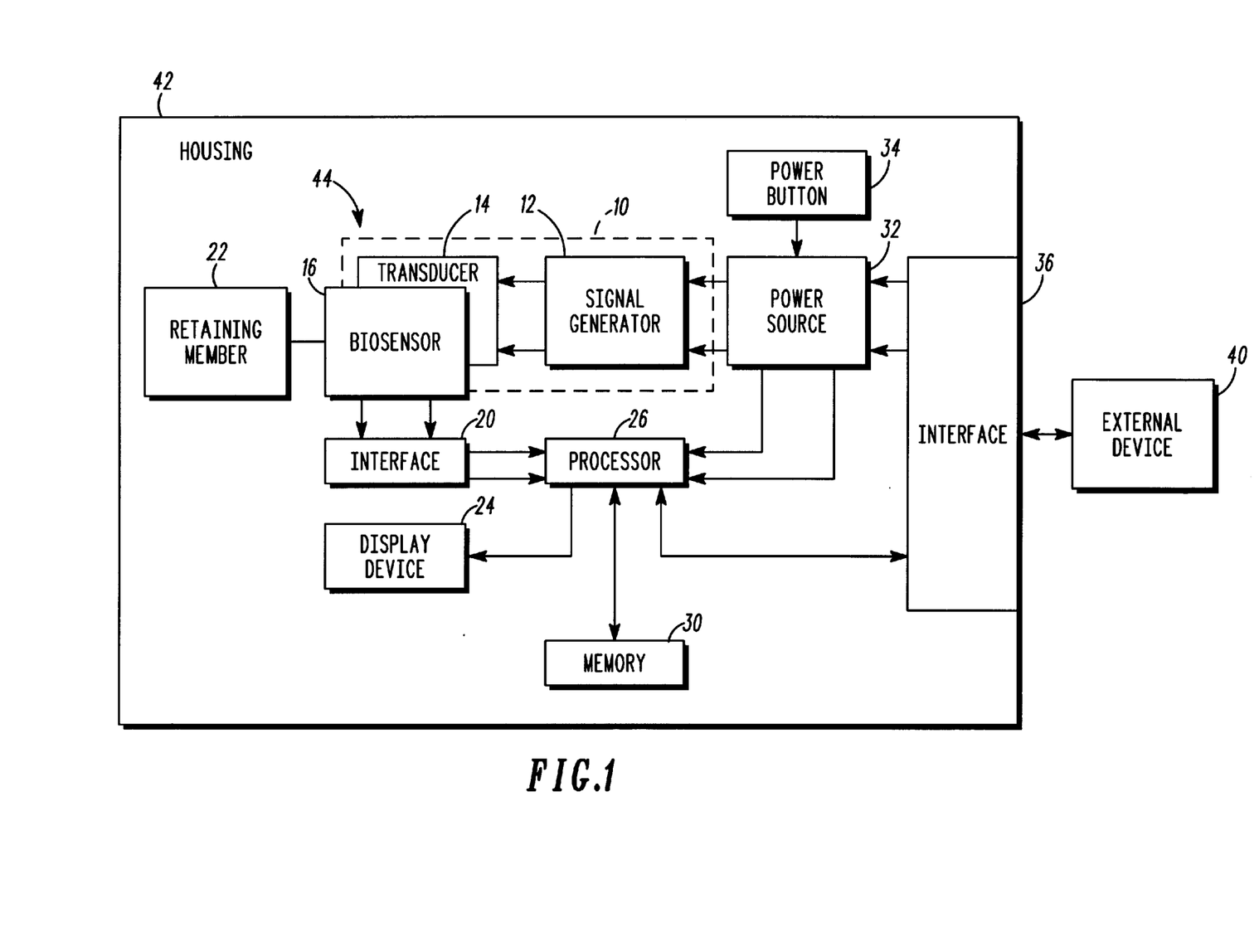
FIG. 1 is a block diagram of a noninvasive apparatus in accordance with the present invention.

FIG. 1 is a block diagram of a noninvasive apparatus in accordance with the present invention. The apparatus includes a noninvasive extraction device 10 to noninvasively extract a biological sample from an end user. Examples of the biological sample include, but are not limited to, blood from the end user and an interstitial fluid from the end user.

Preferably, the noninvasive extraction device 10 extracts the sample through the skin of the end user by transdermal permeation. Alternatively, the noninvasive extraction device 10 can extract the sample through a buccal membrane by transbuccal permeation. Regardless of where the sample is extracted, the noninvasive extraction device 10 extracts the sample without penetrating the skin or another portion of the end user's body.

Preferably, the noninvasive extraction device 10 includes a signal generator 12 and a transducer 14. The signal generator 12 drives the transducer 14 to produce acoustic pressure waves. The acoustic pressure waves enhance and control the permeation of the sample out of the end user's body.

In accordance with the teachings in U.S. Pat. Nos. 4,767,402, 4,780,212, 4,948,587 which are hereby incorporated by reference into this disclosure, it is preferred that the transducer 14 includes an ultrasonic emitter. In this case, the ultrasonic emitter emits an ultrasonic signal having a frequency between 20 kHz and 10 MHz, with a preferred range being between 0.5 MHz and 1.5 MHz. Further, the intensity of the ultrasound signal is selected so as not to burn the end user. In general, the ultrasonic emitter can emit either a pulsed or a continuous ultrasonic signal.

The apparatus further comprises a biosensor 16 to sense a characteristic, property, or parameter of the biological sample. The specific characteristic is dependent upon the biosensor 16 selected in the apparatus. In a first preferred embodiment, the biosensor 16 includes a glucose sensor to sense a measure of glucose in the sample. It is noted that the presence or a level of analytes other than glucose can be sensed using different biosensors. In a second preferred embodiment, the biosensor 16 includes a DNA sensor to sense a DNA sequence in the sample. In a third preferred embodiment, the biosensor 16 includes an HIV sensor.

The biosensor 16 can include a molecular detection device having one or more selective binding sites and/or molecular receptors. In this case, the biosensor 16 preferably includes an imprinted matrix in accordance with U.S. Pat. No. 5,310,648 which is hereby incorporated by reference into the present disclosure. Alternatively, the biosensor 16 can include an imprinted film or member in accordance with any of U.S. Pat. Nos. 5,110,833, 5,310,648, 5,372,719, 5,453,199, 5,461,175, 5,541,342, and 5,587,273 which are hereby incorporated by reference into the present disclosure.

As another alternative, the biosensor 16 can include biological molecular receptors each having a specific affinity to a corresponding molecular structure. For example, each biological molecular receptor can include a chain of a plurality of nucleotides which binds or hybridizes with a molecule having a complementary chain of nucleotides. In this case, each biological molecular receptor can include a DNA probe for detecting a corresponding, complementary DNA sequence in the sample, or an RNA probe for detecting a corresponding, complementary RNA sequence in a sample. As another example, the biological molecular receptor can include an antigen for detecting a corresponding antibody in the sample.

Regardless of its form, the biosensor 16 produces a signal such as an optical signal or an electrical signal in dependence upon the characteristic of the sample. The signal can indicate the presence of the characteristic in the sample, or a measure of the characteristic of the sample. If necessary, the biosensor 16 can include optical or electrical detection means for detecting the binding of sample molecules thereto.

Preferably, the biosensor 16 is adjacent at least a portion of the noninvasive extraction device 10. In this case, it is further preferred that the biosensor 16 covers at least a portion of the noninvasive extraction device 10, such as at least a portion of the transducer 14. As a result, the sample is directly and immediately applied to the biosensor 16 after being noninvasively extracted from the end user. Alternatively, the apparatus can include a sample handling conduit to communicate the sample from the noninvasive extraction device 10 to the biosensor 16.

The apparatus includes an interface 20 to communicate with the biosensor 16. In a preferred embodiment, the interface 20 includes a plurality of electrodes which either capacitively, inductively, or directly couple to the biosensor 16. The biosensor 16 can be permanently integrated with the apparatus or can be removable. The apparatus can include a retaining member 22 which retains a removable biosensor. The retaining member 22 retains the biosensor 16 proximate to at least a portion of the noninvasive extraction device 10.

Optionally, the apparatus includes a display device 24 responsive to the biosensor 20. The display device 24 displays human-readable information associated with the characteristic of the biological sample. The information can include textual information and/or graphical information. The display device 24 can include a plurality of liquid crystal display (LCD) elements or a plurality of light-emitting display (LED) elements to display the information. The display elements can be arranged as an array of pixels or as segments in a segmented display (e.g. a seven-segment display).

Preferably, the display device 24 is responsive to the biosensor 20 via a processor 26. The processor 26 receives data associated with a characteristic, property, or parameter of the sample from the biosensor 20. The processor 26 processes the data to determine the characteristic, property, or parameter of the sample. Thereafter, the processor 26 drives the display device 24 to display information based upon the characteristic. For example, the display device 24 can display a glucose level associated with the sample, a DNA or RNA sequence associated with the sample, or a positive/negative HIV indication associated with the sample.

Additionally, the processor 26 can direct the activation and deactivation of the noninvasive extraction device 10. Further, the processor 26 can control parameters of the noninvasive extraction device 10 such as the frequency, intensity, and duration of the signal emitted by the transducer 14.

The processor 26 can write the data and/or the processed information to a memory 30. Thereafter, the processor 26 can read the data and/or the processed information for subsequent processing or for subsequent display by the display device 24. The memory 30 can also serve to store a program which directs the processor 26 in operating the noninvasive extraction device 10, applying signals to the biosensor 16, processing the data from the biosensor 16, and displaying the information. In general, the memory 30 can include a random-access memory and/or a read-only memory. Preferably, the memory 30 is nonvolatile to maintain its contents in the absence of a powering signal.

The various components of the apparatus are selectively powered by a power source 32. In response to a first user-initiated input received by a power button 34, the power source 32 powers various components to activate the apparatus. In response to a second user-initiated input received by the power button 34, the power source 32 unpowers various components to deactivate the apparatus. The power source 32 can include battery-receiving terminals in contact with a battery. Alternatively, the power source 32 can include a solar cell. As another alternative, the power source 32 can include a plastic battery.

Optionally, the apparatus includes an interface 36 for interfacing with an external device 40. Via the interface 36, the external device 40 can power the various components of the apparatus and/or recharge the battery in the power source 32. Further, data can be communicated between the processor 26 and the external device 40 via the interface 36. For example, the processor 26 can download a software program from the external device 40 to direct the operation of the apparatus. As another example, the processor 26 can communicate sensed data or stored data to the external device 40.

The external device 40 can have various forms. Of particular interest is where the external device 40 includes a computer or a like processing apparatus. In this case, the external device 40 can include a desktop computer, a laptop computer, a palmtop computer, or a personal digital assistant. Alternatively, the external device 40 can include a communication device such as a two-way pager, a telephone, a cellular telephone, or a personal communication system (PCS) telephone. As another alternative, the external device 40 can include a base station or other transceiver in a communication network such as a paging network, a wireless telephone network, a wireless data network, or a satellite network. Other electronic devices are also contemplated for the external device 40.

Dependent upon the external device 40, the interface 36 can include any of: (i) a PCMCIA interface for mating in a PCMCIA slot; (ii) a serial interface for mating with a serial port; (iii) a parallel interface for mating with a parallel port; (iv) a SCSI interface for mating with a SCSI port; (v) an infrared interface for communicating with an infrared port; (vi) a radio frequency transceiver for communicating with a radio frequency port; (vii) a telephone interface for mating with a telephone port; or (viii) an interface for mating with a data port in a wireless telephone. In general, the interface 36 can include any plurality of connectors which mate with a plurality of connectors associated with the external device 40. Additionally, any signal standard can be used to communicate signals between the apparatus and the external device 40.

The apparatus includes a housing 42 to house and/or support the noninvasive extraction device 10, the biosensor 16, the interface 20, the retaining member 22, the display device 24, the processor 26, the memory 30, the power source 32, the power button 34, and the interface 36. Preferably, the housing 42 is sized to be handheld by the end user. It is further preferred that the housing 42 be sized and shaped for carrying within a wallet, a purse, or a pocket of the end user. For these purposes, it is preferred that the housing 42 be card shaped. In this case, for example, the housing 42 can have the size of a credit card, a PCMCIA card, a business card, a smart card, an index card, a trading card, or a playing card.

It is also preferred that the housing 42 be either rigid, semi-rigid, or resilient. The housing 42 can be resilient to deform over a portion of the end user's body when in use, and to recover its shape after use.

Preferably, the housing 42 includes a grasping region 44 for grasping by a hand of the end user. In this case, it is preferred that the noninvasive extraction device 10 extracts the biological sample from a portion of the hand which grasps the grasping region 44. For this purpose, the transducer 14 and the biosensor 16 can be located proximate to the grasping region 44. The portion of the hand from which the sample is extracted can include the thumb, the fingers, the palm, or the back of the hand. In general, however, the noninvasive extraction device 10 can extract the biological sample from any portion of the end user's body including but not limited to his/her arms, legs, and feet.

Figure 2:
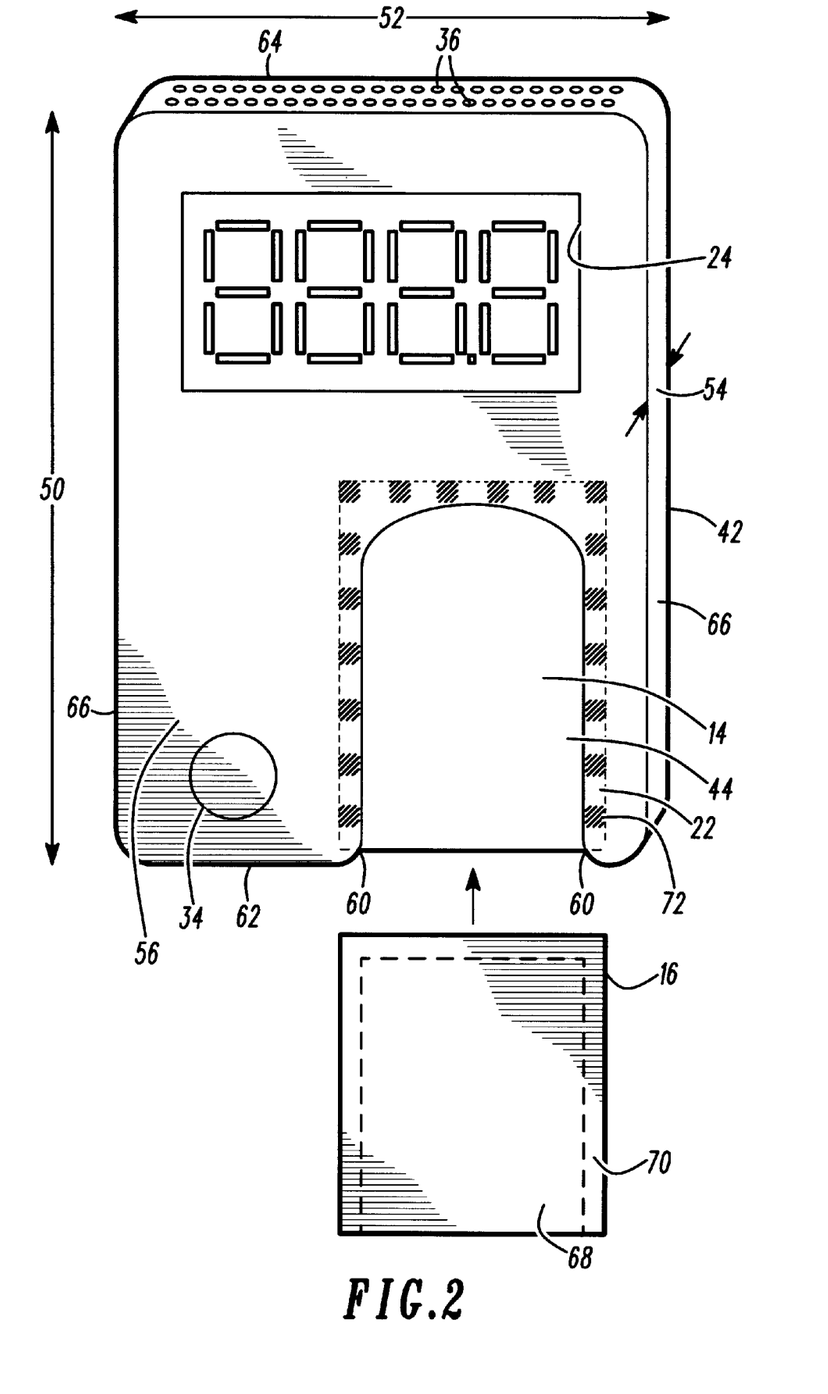
FIG. 2 is a view of a first embodiment of a noninvasive apparatus in accordance with the present invention.

FIG. 2 is a view of a first embodiment of a noninvasive apparatus in accordance with the present invention. In this embodiment, the housing 42 includes a card-shaped housing. The housing 42 is shaped and sized in accordance with a PCMCIA (Personal Computer Memory Card International Association) form standard. The housing 42 has a length 50 of 85.6 mm and a width 52 of 54.0 mm. The housing 42 has a thickness 54 dependent upon the PCMCIA type. For example, the thickness 54 is 3.3 mm for Type I, 5.0 mm for Type II, and 10.5 mm for Type III. Preferably, the housing 42 is rigid or semi-rigid.

The interface 36 comprises a PCMCIA bus connector. In accordance with PCMCIA standards, the interface 36 includes sixty-eight connectors which mate with sixty-eight pins in a mating connector associated with the external device 40. Typically, the external device 40 includes a socket into which the apparatus is inserted to mate the interface 36 thereto. Signals are communicated via the interface 36 in accordance with PCMCIA signal standards.

The housing 42 has a face 56 at which the display device 24 is viewable and at which the grasping region 44 is disposed. At least a portion of the noninvasive extraction device 10, including at least a portion of the transducer 14, is disposed at the grasping region 44 of the face 56. Additionally, the power button 34 is accessible at the face 56.

The housing 42 includes a slot 60 through which the biosensor 16 is inserted and removed. The biosensor 16 can be inserted into the slot 60 at an end 62 of the housing 42 opposite to an end 64 having the interface 36. Alternatively, the slot 60 can receive the biosensor 16 at ends 66 adjacent to the end 64.

When inserted, an interior portion 68 of the biosensor 16 is exposed for contact with the end user while a peripheral portion 70 is retained by the retaining member 22. The interface 20 includes a plurality of electrodes, a representative one being indicated by reference numeral 72, which couple to the peripheral portion 70 when the biosensor 16 is inserted. The biosensor 16 covers at least a portion of the transducer 14, and preferably all of the transducer 14, when inserted. Although illustrated to be rectangular, it is noted that the biosensor 16 can be alternatively shaped.

To use the apparatus, the end user inserts the biosensor 16 through the slot 60 and depresses the power button 34 to activate the apparatus. Thereafter, the end user contacts the interior portion 68 of the biosensor 16 to perform a noninvasive test or diagnostic. Preferably, the end user applies a finger or a thumb to the biosensor 16. In these cases, the apparatus can be supported by a member such as a table top or a wall. Alternatively, the apparatus is grasped by applying a thumb to the biosensor 16 and one or more fingers to an opposite surface of the housing 42.

The noninvasive extraction device 10 facilitates the permeation of the sample through the end user's skin at the grasping region 44. Once extracted, the sample is immediately and directly applied to a surface of the biosensor 16. The processor 26 directs a plurality of conductance measurements to be taken for the biosensor 16. The conductance measurements are taken between a plurality of pairs of the electrodes 72. The processor 26 processes the conductance measurements to determine a characteristic (e.g. a glucose level) associated with the sample. The characteristic is displayed by the display device 24. For example, a numerical indication or a graphical indication of the glucose level can be displayed by the display device 24. Thereafter, the biosensor 16 can be removed through the slot 60.

Figure 3:
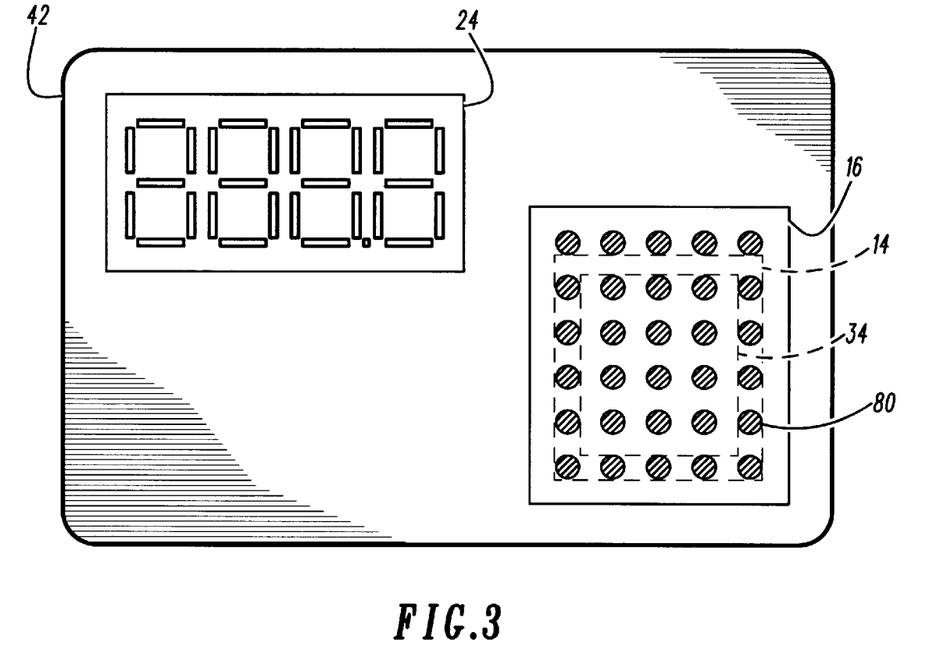
FIG. 3 is a view of a second embodiment of a noninvasive apparatus in accordance with the present invention.

FIG. 3 is a view of a second embodiment of a noninvasive apparatus in accordance with the present invention. In this embodiment, the housing 42 includes a card-shaped substrate. The card-shaped substrate supports the noninvasive extraction device 10 and the biosensor 16. The transducer 14 of the noninvasive extraction device 10 is sandwiched between the biosensor 16 and the substrate. Preferably, the card-shaped substrate is rigid, semi-rigid, or resilient.

The biosensor 16 is permanently integrated with the apparatus. The biosensor 16 is permanently coupled to a plurality of electrodes, a representative one being indicated by reference numeral 80, which comprise the interface 20. The electrodes 80 are arranged as a grid across a bottom surface of the biosensor 16.

The power button 34 is co-located with the transducer 14 and the biosensor 16 to activate the apparatus when the biosensor 16 is depressed by the end user's hand. Preferably, the power button 34 is located beneath the biosensor 16 and the transducer 14.

The card-shaped substrate can comprise a smart card having the display 24, the processor 26 and the power supply 32 integrated therewith. The processor 26 communicates with the biosensor 16 via the electrodes 80.

In use, the apparatus is either supported by a member or grasped by the end user so that a finger or a thumb is applied to the biosensor 16. The end user applies a sufficient force to the biosensor 16 to generate a user-initiated activation signal for the power button 34. In response to the user-initiated activation signal, the noninvasive extraction device 14 is activated to facilitate the permeation of the sample through the end user's skin.

Once extracted, the sample is immediately and directly applied to a surface of the biosensor 16. The processor 26 directs a plurality of conductance or resistance measurements to be taken for the biosensor 16. The conductance or resistance measurements are taken between a plurality of pairs of the electrodes 80. The processor 26 processes the measurements to determine a characteristic (e.g. a glucose level) associated with the sample. The characteristic is displayed by the display device 24. Thereafter, the apparatus can be either disposed or cleaned for a subsequent use. The apparatus can be cleaned with a swab and a cleaning solution such as alcohol. Alternatively, the apparatus can be cleaned electronically if the biosensor 16 is reversible.

Figure 4:
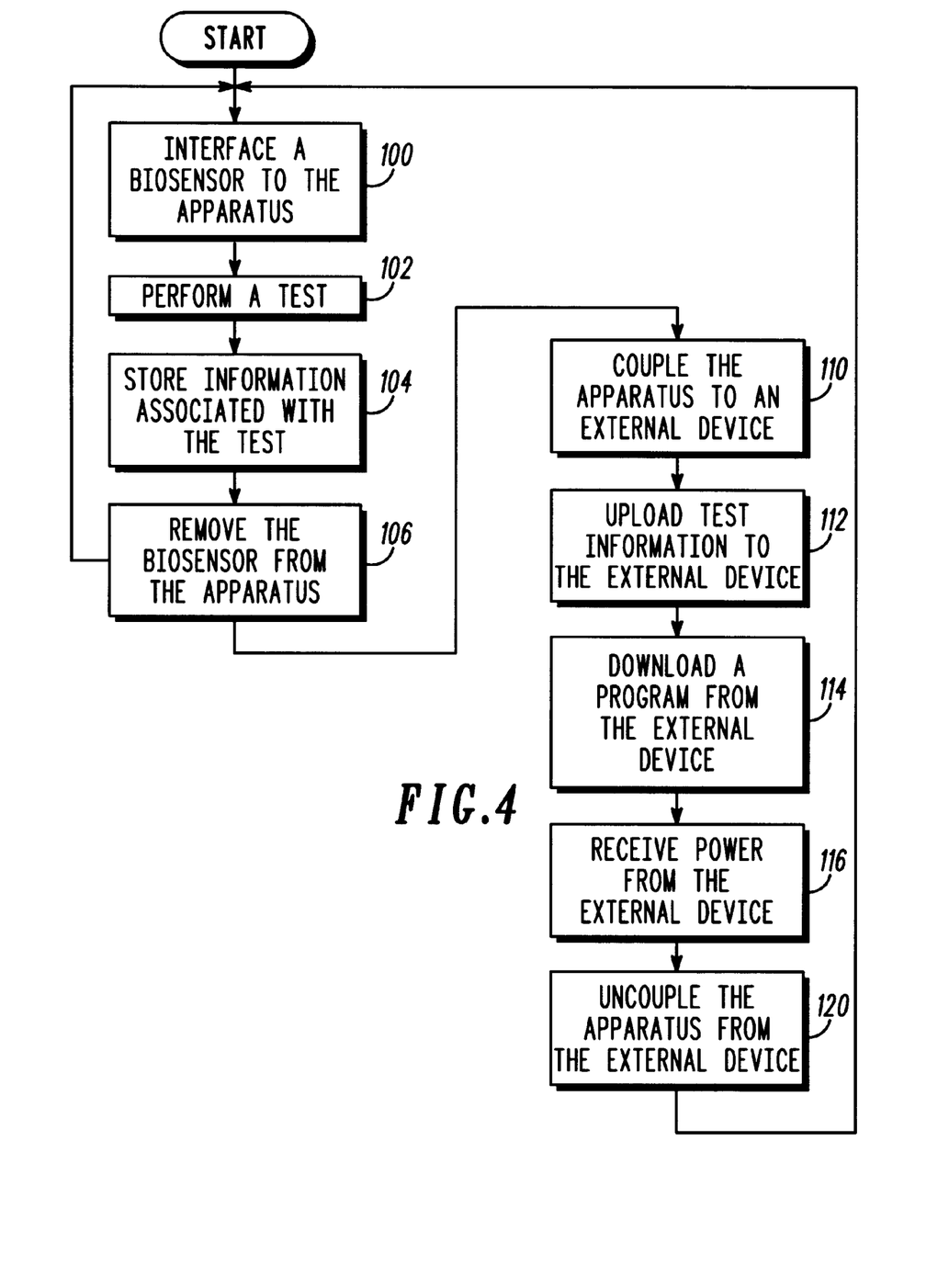
FIG. 4 is a flow chart of a method of using a noninvasive apparatus in accordance with the present invention.

FIG. 4 is a flow chart of a method of using a noninvasive apparatus in accordance with the present invention. As indicated by block 100, if the biosensor 16 is removable, the method optionally includes a step of interfacing the biosensor 16 to the remainder of the apparatus. The biosensor 16 is selected in dependence upon which test is to be performed by the apparatus.

As indicated by block 102, the method includes a step of performing the test using the apparatus. The step of performing the test includes noninvasively extracting the sample from the end user, optionally communicating the sample to the biosensor 16, sensing data associated with the sample with the biosensor 16, processing the data to determine a characteristic of the sample, and displaying an indication of the characteristic.

As indicated by block 104, the method optionally includes a step of storing information associated with the sample to the memory 30. The information can include the data associated with the sample and/or the characteristic of the sample. Preferably, this step further includes storing a time and a date associated with the test.

As indicated by block 106, the method optionally includes a step of removing the biosensor 16 from the remainder of the apparatus. The biosensor 16 can be disposed after a single use, or cleaned for a subsequent use.

Flow of the method can return back to block 100 to perform one or more subsequent tests. For example, in a glucose meter embodiment of the apparatus, an end user may perform three or four glucose tests over the course of a day.

Thereafter, flow of the method proceeds to block 110 which indicates a step of coupling the apparatus to the external device 40. The step of coupling can include coupling the interface 36 and the external device 40 by a wireline connection. For example, the step of coupling can include inserting the PCMCIA card embodiment of FIG. 2 into a PCMCIA socket associated with the external device 40. Alternatively, the step of coupling can include coupling the interface 36 and the external device 40 by a wireless link. The wireless link can include an infrared link or a radio frequency link.

As indicated by block 112, the method optionally includes a step of uploading the test information from the apparatus to the external device 40. The test information is retrieved from the memory 30 by the processor 26, and communicated to the interface 36. A signal representative of the test information is communicated from the interface 36 to the external device 40.

As indicated by block 114, the method optionally includes a step of downloading a program from the external device 40 to the apparatus. The program directs the operation of the apparatus in performing subsequent tests. The interface 36 receives a signal representative of the program from the external device 40. The interface 36 communicates the program to the processor 26. The processor 26 stores the program in the memory 30.

As indicated by block 116, the method optionally includes a step of powering the apparatus while the apparatus is linked to the external device 40. This step can include recharging the power source 32 by a current received via the interface 36.

As indicated by block 120, the method optionally includes a step of uncoupling the apparatus from the external device 40. The step of uncoupling can include uncoupling a wireline connection between the interface 36 and the external device 40. For example, the PCMCIA card embodiment of FIG. 2 can be removed from a PCMCIA socket associated with the external device 40.

Flow of the method is directed back to block 100 to perform one or more subsequent tests. The subsequent tests can be performed in accordance with the program downloaded in the step indicated by block 114. The programmability of the apparatus advantageously allows a plurality of different tests to be performed using a single apparatus. The test is performed by downloading the program and inserting a specific biosensor therefor.

Figure 5:
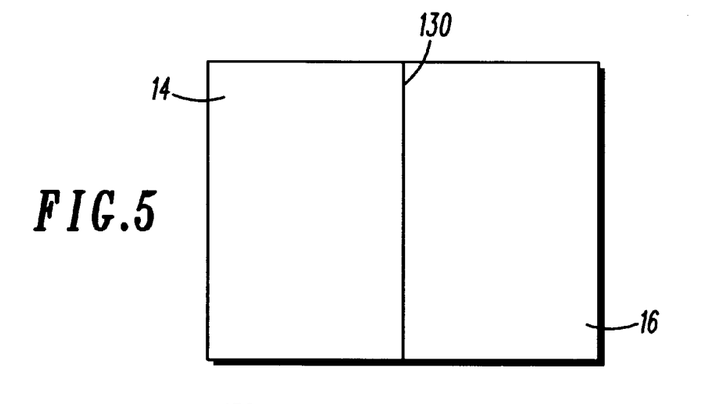
FIG. 5 is a view of a first alternative configuration of the transducer and the biosensor for embodiments of the present invention.

FIG. 5 is a view of a first alternative configuration of the transducer 14 and the biosensor 16 for embodiments of the present invention. In this configuration, the biosensor 16 is adjacent a side 130 of the transducer 14. Preferably, the biosensor 16 and the transducer 14 are oriented to be substantially coplanar.

One approach to using this configuration includes the end user rolling or sliding his/her finger or thumb from the transducer 14 to the biosensor 16. In this approach, the transducer 14 promotes the noninvasive extraction of the sample, and the sample is deposited onto the biosensor 16 thereafter.

Figure 6:
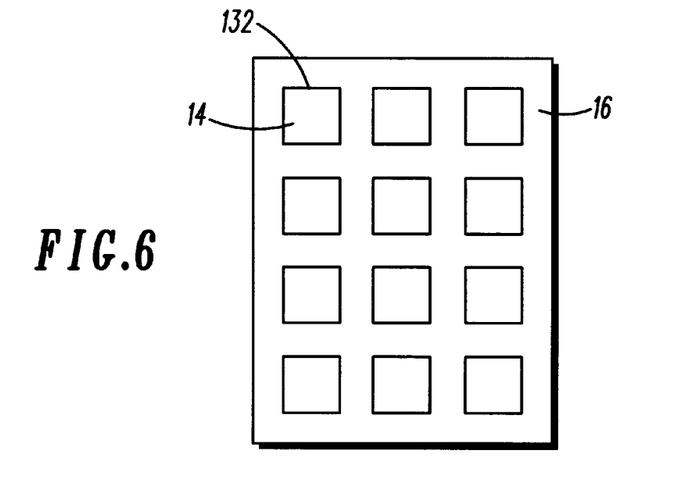
FIG. 6 is a view of a second alternative configuration of the transducer and the biosensor for embodiments of the present invention.

FIG. 6 is a view of a second alternative configuration of the transducer 14 and the biosensor 16 for embodiments of the present invention. In this configuration, the biosensor 16 masks at least a portion of the transducer 14. In particular, the biosensor 16 masks all of the transducer 14 but a plurality of holes. A representative one of the holes is indicated by reference numeral 132. The holes provide paths for directly exposing portions of the end user's body to the noninvasive extraction device 10. For example, the holes provide paths for directly applying ultrasonic signals to portions of the end user's body.

Figure 7:
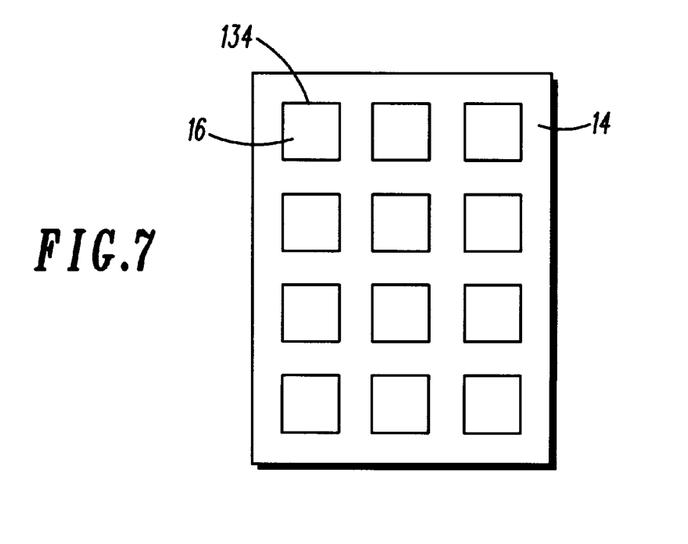
FIG. 7 is a view of a third alternative configuration of the transducer and the biosensor for embodiments of the present invention.

FIG. 7 is a view of a third alternative configuration of the transducer 14 and the biosensor 16 for embodiments of the present invention. In this configuration, the biosensor 16 includes a plurality of biosensors, a representative one of the biosensors being indicated by reference numeral 134. The biosensors mask portions of the transducer 14. By not masking all of the transducer 14, the noninvasive extraction device 10 can directly access portions of the end user's body. For example, the ultrasonic signal can be directly applied to portions of the end user's body unmasked by the biosensors.

It is noted that noninvasive extraction devices other than the preferred embodiments described herein can be used in alternative embodiments of the present invention. For example, the noninvasive extraction device can alternatively include a vacuum which draws the sample through the skin of the end user.

It is also noted that measurements other than the herein-described conductance measurements can be used to sense a characteristic of the sample. Examples of other measurements include, but are not limited to, voltage measurements, current measurements, impedance measurements, and optical measurements.

It is also noted that the herein-described embodiments of the present invention can be modified for use in drug delivery applications. In this case, the noninvasive extraction device is either replaced by or utilized as a drug delivery device. Preferably, the drug delivery device includes the signal generator 12 and the transducer 14 to emit ultrasonic signals as described earlier. The biosensor 16 is replaced by a member which supports a therapeutic material such as pharmaceutical material, a drug, a medicine, a protein, insulin, or hormones. The therapeutic material permeates into the body of the end user in response to the ultrasonic signals produced by the transducer 14.

Thus, there has been described herein several embodiments including preferred embodiments of a noninvasive apparatus.

Because the various embodiments of the present invention noninvasively extract a biological sample from a hand at a grasping region, they provide a significant improvement in extracting the sample while the end user is holding the apparatus.

Additionally, by supporting a noninvasive extraction device with a card-shaped housing, embodiments of the apparatus can be carried in a pocket, purse, or wallet of an end user. A PCMCIA card housing with a PCMCIA connector further facilitates interfacing the apparatus with an external device having a PCMCIA socket.

Further, by receiving a removable biosensing module for use with the noninvasive apparatus, biosensors can be disposed and replaced after a single-use. Also, the noninvasive apparatus can perform any of a variety of tests based upon which biosensor is installed. A program which dictates the test can be downloaded from an external device.

Still further, by uploading test information from the apparatus to an external device, the external device can process, communicate, and/or archive the information.

It will be apparent to those skilled in the art that the disclosed invention may be modified in numerous ways and may assume many embodiments other than the preferred form specifically set out and described above.

Accordingly, it is intended by the appended claims to cover all modifications of the invention which fall within the true spirit and scope of the invention.

What is claimed is:

1. An apparatus which cooperates with a removable biosensor, the apparatus comprising:

a noninvasive extraction device to noninvasively extract a biological sample;

a retaining member to retain the removable biosensor proximate to at least a portion of the noninvasive extraction device, the retaining member to cover a first portion of a surface of the removable biosensor while exposing a second portion of the surface of the removable biosensor for user contact, the removable biosensor to sense a characteristic of the biological sample;

a first set of at least two electrodes to couple to the removable biosensor near a first edge of the removable biosensor covered by the retaining member; and a second set of at least two electrodes to couple to the removable biosensor near a second edge of the removable biosensor covered by the retaining member.

2. The apparatus of claim 1 wherein the first portion comprises a peripheral portion of the surface of the removable biosensor.

3. The apparatus of claim 2 wherein the second portion comprises a central portion of the surface of the removable biosensor.

4. The apparatus of claim 1 wherein the noninvasive extraction device includes an ultrasonic emitter.

5. The apparatus of claim 1 wherein the removable biosensor covers at least a portion of the noninvasive extraction device when retained by the retaining member.

6. The apparatus of claim 1 further comprising a third set of at least two electrodes to couple to the removable biosensor near a third edge of the removable biosensor covered by the retaining member.

7. The apparatus of claim 1 further comprising a card-shaped housing supporting the noninvasive extraction device and the retaining member.

8. The apparatus of claim 1 further comprising:

an interface; and a processor to receive a program from an external device via the interface, the processor to direct the noninvasive extraction device and to process data from the biosensor in accordance with the program.

9. An apparatus which cooperates with a removable biosensor, the apparatus comprising:

a card-shaped housing having a length of about 85.6 mm and a width of about 54 mm;

a noninvasive extraction device supported by the card-shaped housing to noninvasively extract a biological sample;

a retaining member to retain the removable biosensor proximate to at least a portion of the noninvasive extraction device, the retaining member to cover a first portion of a surface of the removable biosensor while exposing a second portion of the surface of the removable biosensor for user contact, the removable biosensor to sense a characteristic of the biological sample;

a first set of at least two electrodes to couple to the removable biosensor near a first edge of the removable biosensor covered by the retaining member; and a second set of at least two electrodes to couple to the removable biosensor near a second edge of the removable biosensor covered by the retaining member.

* * * * *